(12) United States Patent
Stursa et al.

(10) Patent No.: US 10,596,348 B2
(45) Date of Patent: Mar. 24, 2020

(54) CONDUCTIVE TIP CATHETER

(71) Applicant: Teleflex Medical Incorporated, Morrisville, NC (US)

(72) Inventors: Radek Stursa, Trebechovice pod Orebem (CZ); Petr Streda, Sveti (CZ)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 401 days.

(21) Appl. No.: 15/210,362

(22) Filed: Jul. 14, 2016

(65) Prior Publication Data

US 2017/0014598 A1    Jan. 19, 2017

Related U.S. Application Data

(60) Provisional application No. 62/192,574, filed on Jul. 15, 2015.

(51) Int. Cl.
*A61M 25/00* (2006.01)
*A61M 19/00* (2006.01)
(Continued)

(52) U.S. Cl.
CPC ...... *A61M 25/0068* (2013.01); *A61M 25/005* (2013.01); *A61M 25/0012* (2013.01);
(Continued)

(58) Field of Classification Search
CPC .......... A61M 19/00; A61M 2025/0008; A61M 2025/0018; A61M 2025/0081; A61M 25/005; A61M 25/0053; A61M 25/0054; A61M 25/0069; A61M 25/008; A61M 25/0012; A61M 25/0067; A61M 25/0068; A61M 25/0082; A61M 2025/0058; A61M 2205/0233
See application file for complete search history.

(56) References Cited

U.S. PATENT DOCUMENTS 4,759,378 A    7/1988  Swendson et al.
4,769,006 A    9/1988  Papantonakos
(Continued)

FOREIGN PATENT DOCUMENTS

JP    2004305735 A    11/2004
JP    2007502197 A     2/2007
(Continued)

*Primary Examiner* — Shefali D Patel
(74) *Attorney, Agent, or Firm* — Baker & Hostetler LLP

(57) ABSTRACT

A conductive tip catheter includes a flexible tubular member defining a lumen that extends between a proximal end and a distal end. The conductive tip catheter also includes an electrically conductive metallic coil at least partially located within the lumen of the flexible tubular member. The electrically conductive metallic coil includes a first region located at a distal end of the metallic coil and having a first pitch, a second region proximal to the first region and having a second pitch that is greater than the first pitch, and a third region proximal to the second region and having a third pitch that is different from the first pitch and the second pitch. A conductive tip is located at the distal end of the flexible tubular member, and the conductive tip defines a tip lumen in fluid communication with the lumen.

22 Claims, 4 Drawing Sheets

(51) Int. Cl.
  *A61N 1/05* (2006.01)
  *A61N 1/36* (2006.01)
  *A61B 90/00* (2016.01)

(52) U.S. Cl.
  CPC .... *A61M 25/0053* (2013.01); *A61M 25/0067* (2013.01); *A61M 25/0069* (2013.01); *A61B 2090/062* (2016.02); *A61B 2090/3937* (2016.02); *A61M 19/00* (2013.01); *A61M 25/0017* (2013.01); *A61M 25/0082* (2013.01); *A61M 2025/0058* (2013.01); *A61M 2205/0233* (2013.01); *A61N 1/0551* (2013.01); *A61N 1/36017* (2013.01); *A61N 1/36021* (2013.01)

(56) References Cited

U.S. PATENT DOCUMENTS

| | | | |
|---|---|---|---|
| 4,938,822 A | 7/1990 | Peers-Trevarton | |
| 5,336,222 A | 8/1994 | Durgin, Jr. et al. | |
| 5,484,425 A | 1/1996 | Fischell et al. | |
| 5,782,760 A | 7/1998 | Schaer | |
| 5,800,496 A | 9/1998 | Swoyer et al. | |
| 6,123,718 A * | 9/2000 | Tu | A61B 18/1492 606/41 |
| 6,451,005 B1 * | 9/2002 | Saitou | A61M 25/0053 604/526 |
| 7,027,873 B2 | 4/2006 | Pajunk et al. | |
| 7,386,341 B2 * | 6/2008 | Hafer | A61B 17/3401 607/3 |
| 7,899,552 B2 | 3/2011 | Atanasoska et al. | |
| 8,636,724 B2 | 1/2014 | Wiita et al. | |
| 2004/0210295 A1 | 10/2004 | Brushey | |
| 2006/0064123 A1 | 3/2006 | Bonnette et al. | |
| 2007/0021771 A1 | 1/2007 | Oepen et al. | |
| 2007/0265516 A1 * | 11/2007 | Wang | A61B 5/0402 600/374 |
| 2014/0316327 A1 | 10/2014 | Rajendran et al. | |
| 2016/0144157 A1 * | 5/2016 | Gulachenski | A61M 25/10185 604/99.02 |

FOREIGN PATENT DOCUMENTS

| | | |
|---|---|---|
| JP | 2007236472 A | 9/2007 |
| JP | 2008538997 A | 11/2008 |
| JP | 2011120845 A | 6/2011 |
| JP | 2014200330 A | 10/2014 |

* cited by examiner

CONDUCTIVE TIP CATHETER

CROSS-REFERENCE TO RELATED APPLICATIONS

This application claims priority to U.S. provisional patent application No. 62/192,574, entitled "Conductive Tip Catheter," filed Jul. 15, 2015, the disclosure of which is hereby incorporated by reference in its entirety.

FIELD OF THE DISCLOSURE

This disclosure generally relates to a conductive tip catheter. Specifically, this disclosure relates to a conductive tip catheter for administering anesthesia.

BACKGROUND

Peripheral nerve block catheters are widely used for the administration of surgical anesthesia as well as post-operative and nonsurgical anesthesia. A peripheral nerve block catheter is inserted through a needle into a desired location in a patient's tissue along the patient's nerve. Anesthesia is then injected through the openings at the distal end of the catheter into the nerve location to selectively numb the desired location to reduce pain. These catheters sometimes include a conductor to allow nerve stimulation by electrical impulses.

Often these peripheral nerve block catheters are inserted into the nerve location for an extended period of time, especially during post-operative pain treatment. During this time, tissue growth may occur at openings of the catheter, such as between exposed coils on the device. This tissue growth may restrict flow of anesthetic from the catheter and result in tissue and nerve damage when the catheter is ultimately removed from the patient.

Accordingly, there is a need for an improved conductive tip catheter to administer anesthesia and prevent the growth of tissue during extended dwell procedures.

SUMMARY OF THE DISCLOSURE

The foregoing needs are met, to a great extent, by the conductive tip catheter described below. The conductive tip catheter includes a flexible tubular member having a proximal end and a distal end. The flexible tubular member defines a lumen extending between the proximal end and the distal end. The conductive tip catheter also includes an electrically conductive metallic coil at least partially located within the lumen of the flexible tubular member. The electrically conductive metallic coil includes a first region located at a distal end of the metallic coil having a first pitch, a second region proximal to the first region having a second pitch that is greater than the first pitch, and a third region proximal to the second region having a third pitch that is different from the first pitch and the second pitch. The conductive tip catheter also includes a conductive tip located at the distal end of the flexible tubular member. The conductive tip defines a tip lumen in fluid communication with the lumen.

In some aspects, the conductive tip may include a conductive polymer. In particular, the conductive polymer may be carbon-filled polyurethane. The first region of the electrically conductive metallic coil can extend distally from the distal end of the flexible tubular member. The conductive tip can be welded to the first region of the electrically conductive metallic coil. Further, the conductive tip can be welded over the first region of the electrically conductive metallic coil. In particular, the conductive tip can be radio frequency welded over the first region of the electrically conductive metallic coil.

In some aspects, an inner diameter of the tip lumen may be smaller than an outer diameter of the first region of the electrically conductive metallic coil. An inner diameter of the tip lumen can also be equal to an outer diameter of the first region of the electrically conductive metallic coil. The flexible tubular member may include polyurethane. The conductive tip catheter can include a safety ribbon located within the lumen of the flexible tubular member. The safety ribbon can include a metallic wire. The safety ribbon can be coupled to the electrically conductive metallic coil at a distal region of the electrically conductive metallic coil and a proximal region of the electrically conductive metallic coil.

In some aspects, the flexible tubular member can include a plurality of depth markers on an exterior surface of the flexible tubular member. The conductive tip can have a rounded distal end. A proximal end of the electrically conductive metallic coil can extend proximally from the proximal end of the flexible tubular member. The proximal end of the electrically conductive metallic coil can be connected to an electrical current source. The electrically conductive metallic coil may directly connects to the flexible tubular member at each point of contact between the electrically conductive metallic coil and the flexible tubular member.

In some aspects, the third pitch may be less than the second pitch. The third pitch may also be greater than the first pitch. The electrically conductive metallic coil can include a fourth region proximal to the third region having a fourth pitch that is greater than the third pitch. The electrically conductive metallic coil can also include a fifth region proximal to the fourth region having a fifth pitch that is less than the fourth pitch. A proximal end of the conductive tip catheter can be connected to a fluid source in fluid communication with the lumen of the flexible tubular member. The fluid source can be an anesthetic.

In some aspects, a conductive tip catheter includes a flexible tubular member having a proximal end and a distal end. The flexible tubular member defines a lumen extending between the proximal end and the distal end. The conductive tip catheter also includes an electrically conductive metallic coil at least partially located within the lumen of the flexible tubular member. The metallic coil includes a first region located at a distal end of the metallic coil having a first pitch, a second region proximal to the first region having a second pitch that is greater than the first pitch, and a third region proximal to the second region having a third pitch that is less than the second pitch. The conductive tip catheter also includes a conductive tip made from carbon-filled polyurethane and welded over the first region of the metallic coil through radio frequency welding. The conductive tip defines a tip lumen in fluid communication with the lumen. The conductive tip catheter also includes a safety ribbon located within the lumen of the flexible tubular member. The safety ribbon is coupled to the electrically conductive metallic coil at a distal region of the electrically conductive metallic coil and a proximal region of the electrically conductive metallic coil. The electrically conductive metallic coil directly connects to the flexible tubular member at each point of contact between the electrically conductive metallic coil and the flexible tubular member.

Certain aspects of the conductive tip catheter device have been outlined such that the detailed description thereof herein may be better understood. There are, of course, additional aspects of the disclosure that will be described below. In this respect, before explaining at least one aspect of the conductive tip catheter in detail, it is to be understood that the conductive tip catheter is not limited in its application to the details of construction and to the arrangements of the components set forth in the following description or illustrated in the drawings. The conductive tip catheter is capable of functions in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the disclosure. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the disclosure are illustrated by way of examples in the accompanying drawings.

In the drawings, like reference numbers and numerals indicate like parts throughout the various views, except where indicated otherwise.

DETAILED DESCRIPTION

Figure 1:
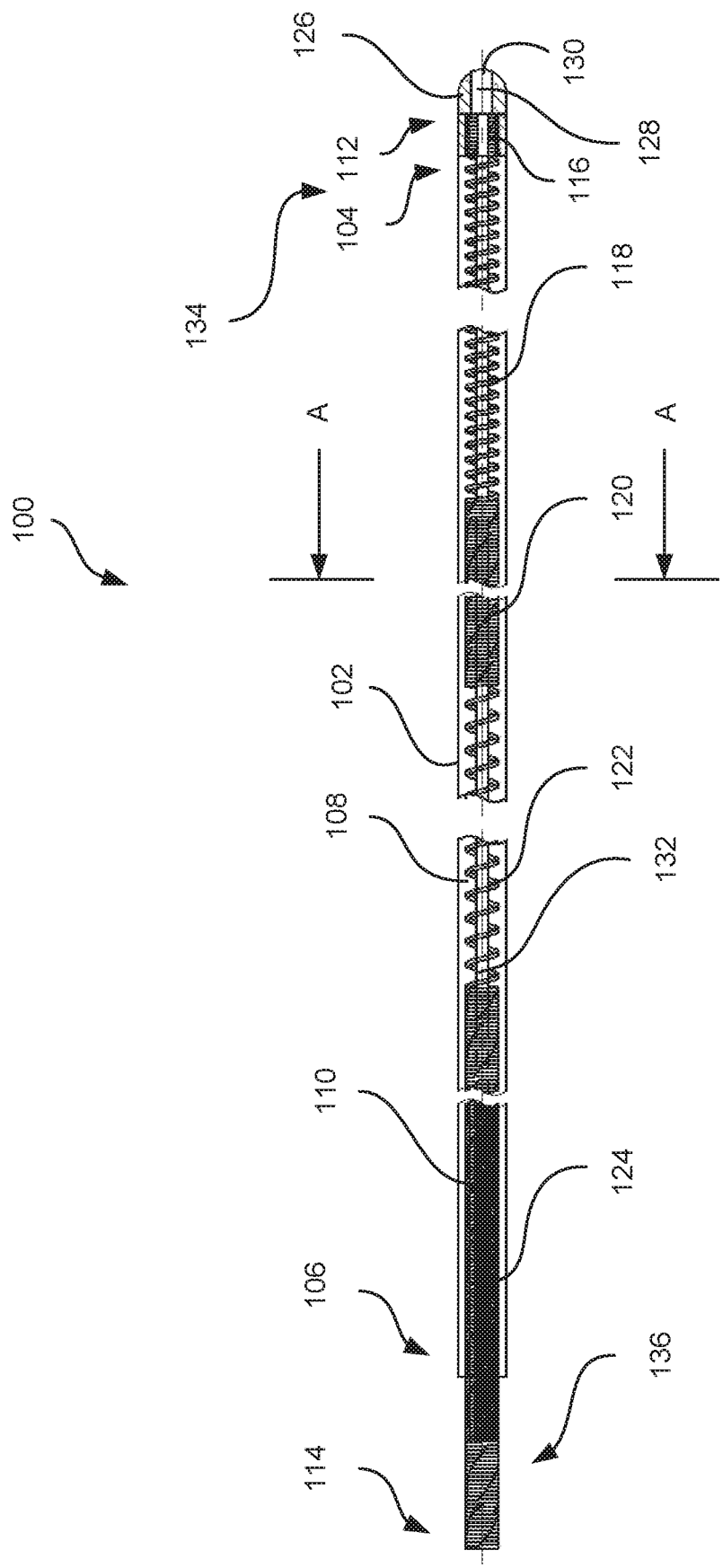
FIG. 1 is a side view of a conductive tip catheter, according to an aspect of the disclosure.

FIG. 1 is a side view of a conductive tip catheter 100, according to an aspect of the present disclosure. The conductive tip catheter 100 includes a flexible tubular member 102 having a distal end 104 and a proximal end 106. The flexible tubular member 102 defines a lumen 108 that extends from the proximal end 106 to the distal end 104. The proximal end 106 of the flexible tubular member 102 may be connected to a fluid source (not shown) in fluid communication with the lumen 108. The fluid source may be a source of an anesthetic for use during or after surgery. The flexible tubular member 102 may be made from a thermosetting polymer or a thermoplastic including polyurethane, polyester resins, polyimides, polyethylene, polyvinyl chloride, polypropylene, and/or polyamide. In particular, the flexible tubular member 102 can be extruded thermoplastic polyurethane.

The conductive tip catheter 100 also includes a metallic coil 110. The metallic coil 110 is electrically conductive and may be located within the lumen 108 of the flexible tubular member 102. The metallic coil 110 extends from a distal end 112 to a proximal end 114 thereof. The proximal end 114 of the metallic coil 110 may be connected to an electrical current source for providing electrical stimulation once the conductive tip catheter is inserted into a patient. The metallic coil 110 may be made from stainless steel or another corrosion resistant metallic compound such as titanium, aluminum, and/or platinum.

The metallic coil 110 may be coupled to the flexible tubular member 102 such that the metallic coil 110 may not be able to move laterally relative to the flexible tubular member 102. The metallic coil 110 may be coupled to the flexible tubular member 102 at select regions of the metallic coil 110 or along the entire length of the metallic coil 110. The metallic coil 110 may be coupled to the flexible tubular member 102 by welding, an adhesive, solvent swelling, or another method known in the art. In a preferred aspect, the flexible tubular member 102 is coupled to the metallic coil 110 using solvent swelling with tetrahydrofuran and heptane. The solvent swelling process allows the flexible tubular member 102 to be tightened around and bonded to the metallic coil 110 without the need for any adhesives. The solvent swelling process may allow the metallic coil 110 to directly connect to the flexible tubular member 102 at each point of contact between the metallic coil 110 and flexible tubular member 102.

The metallic coil 110 may be partially located within the lumen 108 of the flexible tubular member 102. The distal end 112 of the metallic coil 110 may extend distally from the distal end 104 of the flexible tubular member 102. Similarly, the proximal end 114 of the metallic coil 110 may extend proximally from the proximal end 106 of the flexible tubular member 102. That is, the flexible tubular member 102 may not overlap with the distal end 112 and/or proximal end 114 of the metallic coil 110. As such, the length of the metallic coil 110 may be greater than the length of the flexible tubular member 102.

The metallic coil 110 includes a plurality of regions having different pitches. In one aspect illustrated in FIG. 1, the metallic coil 110 includes a first region 116 having a first pitch, a second region 118 having a second pitch, a third region 120 having a third pitch, a fourth region 122 having a fourth pitch, and a fifth region 124 having a fifth pitch. In other aspects, a metallic coil 110 may have fewer than five regions or more than five regions with each region having a different pitch. In addition to the specific aspects mentioned below, the conductive tip catheter 100 may be implemented with other configurations of length and pitch for the plurality of regions of the metallic coil 110. FIG. 1 does not illustrate the plurality of regions to scale.

The first region 116 may extend from the distal end 112 of the metallic coil 110. The first region 116 may have a length between 0.5 and 2 mm, such as, for example, 1 mm. The first region 116 may also have a first pitch with a low pitch distance, such as, for example, between 0.001 mm and 0.05 mm. The low first pitch of the first region 116 may allow the distal end 112 of the metallic coil 110 to be more rigid. The more rigid distal end 112 may assist in the insertion and/or maneuvering of the conductive tip catheter 100 during use.

The second region 118 is located proximal to the first region 116. The second region 118 may have a length greater than that of the first region 116. For example, the second region 118 may have a length between 10 mm and 25 mm, such as, for example, 19 mm. The second pitch of the second region 118 may be greater than the first pitch of the first region 116. For example, the second pitch may be between 0.1 and 0.5 mm, such as, for example, 0.3 mm. The larger second pitch may allow the second region 118 of the metallic coil 110 to be more flexible relative to the first region 116.

The third region 120 is located proximal to the second region 118. The third region 120 may have a length greater than that of the second region 118. For example, the third region 120 may have a length between 100 and 250 mm, such as, for example, 180 mm. The third pitch of the third region 120 may be less than the second pitch of the second region 118. For example, the third pitch may be between, for example, 0.001 mm and 0.05 mm. The third pitch may be roughly equivalent to the first pitch, or may be greater than or less than the first pitch.

The fourth region 122 is located proximal to the third region 120. The fourth region 122 may have a length less than that of the third region 120. For example, the fourth region 122 may have a length between 5 mm and 25 mm, such as, for example, 15 mm. The fourth pitch of the fourth region 122 may be greater than the third pitch of the third region 120. For example, the fourth pitch may be between 0.1 and 0.8 mm, such as, for example, 0.45 mm. The fourth pitch may be roughly equivalent to the second pitch, or greater than or less than the second pitch. A magnitude of the fourth pitch may be sufficient to allow a user to view a fluid level within the lumen 108 of the flexible tubular member 102, such that the fourth region 122 provides a flashback window. In other aspects, the conductive tip catheter 100 may include additional distal windows of varying sizes along the metallic coil 110.

The fifth region 124 is located proximal to the fourth region 122. The fifth region 124 may extend from a proximal end of the fourth region 122 to the proximal end 114 of the metallic coil 110. The fifth region 124 may have a length greater than that of the fourth region 122. For example, the fifth region 124 may have a length between 200 mm and 800 mm, such as, for example, 400 mm. The fifth pitch of the fifth region 124 may be less than the fourth pitch of the fourth region 122. For example, the fifth pitch may be between 0.001 mm and 0.05 mm. The fifth pitch may be roughly equivalent to the first pitch of the first region 116 and/or the third pitch of the third region 120. Alternatively, the fifth pitch may be greater than or less than the first pitch of the first region 116 and/or the third pitch of the third region 120.

Figure 2:
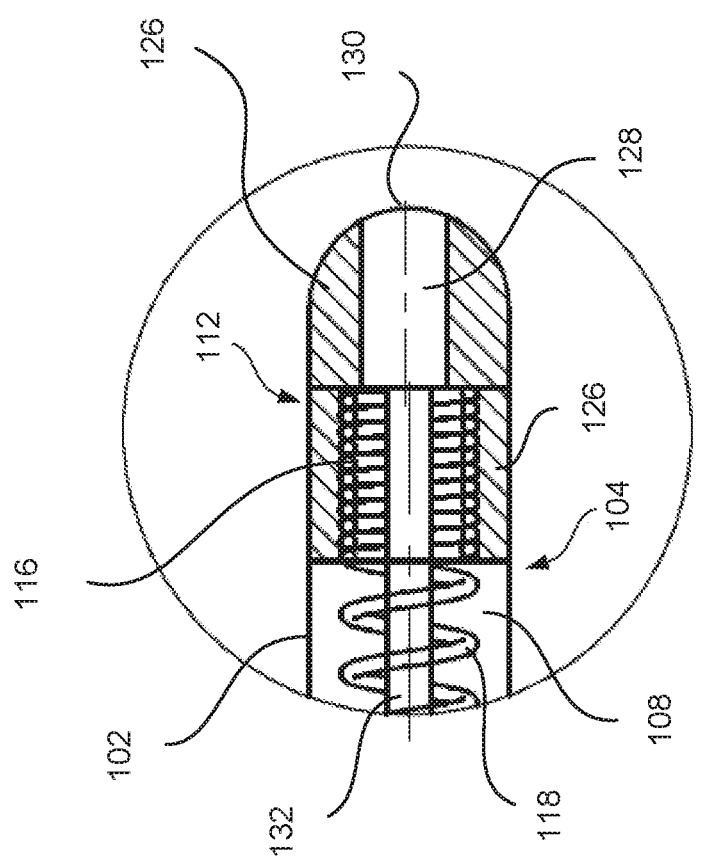
FIG. 2 is an enlarged view of a portion of FIG. 1 illustrating a conductive tip, according to an aspect of the present disclosure.

As illustrated in FIG. 1, the conductive tip catheter 100 also includes a conductive tip 126. FIG. 2 is an enlarged view of a portion of FIG. 1 illustrating the conductive tip 126, according to an aspect of the present disclosure. As illustrated in FIG. 2, the conductive tip 126 may have a rounded distal end 130. The conductive tip 126 may be located distal to the distal end 112 of the metallic coil 110. In particular, the conductive tip 126 may be located distal to the first region 116 of the metallic coil 110. The conductive tip 126 may be coupled to the metallic coil 110 by welding, such as induction welding, radio frequency welding, and ultrasonic welding, by an adhesive, and/or using another method known in the art. The conductive tip 126 may be welded over the first region 116 of the metallic coil 110. That is, a proximal region of the conductive tip 126 is bonded around an exterior surface of the first region 116 of the metallic coil 110.

The conductive tip 126 defines a tip lumen 128 which is in fluid communication with the lumen 108 of the flexible tubular member 102. As illustrated in FIG. 2, the tip lumen 128 may be open at the distal end 130 of the conductive tip 126 and allow fluid to flow from the lumen 108 of the flexible tubular member 102 through the tip lumen 128 and out of the conductive tip 126. The tip lumen 128 may have an inner diameter less than an inner diameter of the lumen 108 of the flexible tubular member 102. The tip lumen 128 may also have an inner diameter less than, greater than, or equal to an outer diameter of the first region 116 of the metallic coil 110. For example, the inner diameter of the tip lumen 128 is less than an outer diameter of the first region 116 of the metallic coil 110 as illustrated in FIGS. 1 and 2. The conductive tip 126 may be made from a conductive polymer including polypyrroles, polythiphenes, polyanilines, doped polymers, such as, for example, carbon-filled polyurethane.

As illustrated in FIGS. 1 and 2, conductive tip catheter 100 may include a safety ribbon 132. The safety ribbon 132 is located within the lumen 108 of the flexible tubular member 102. The safety ribbon 132 may be a metal wire made from stainless steel. The safety ribbon 132 may be coupled to the metallic coil 110 at a distal region 134 and/or proximal region 136 of the metallic coil 110. Alternatively, the safety ribbon 132 may be coupled to the metallic coil 110 at a plurality of points that span between the distal end 112 and proximal end 114 of the metallic coil 110. The safety ribbon 132 may be coupled to the metallic coil 110 by welding, an adhesive, or another method known in the art.

Figure 3:
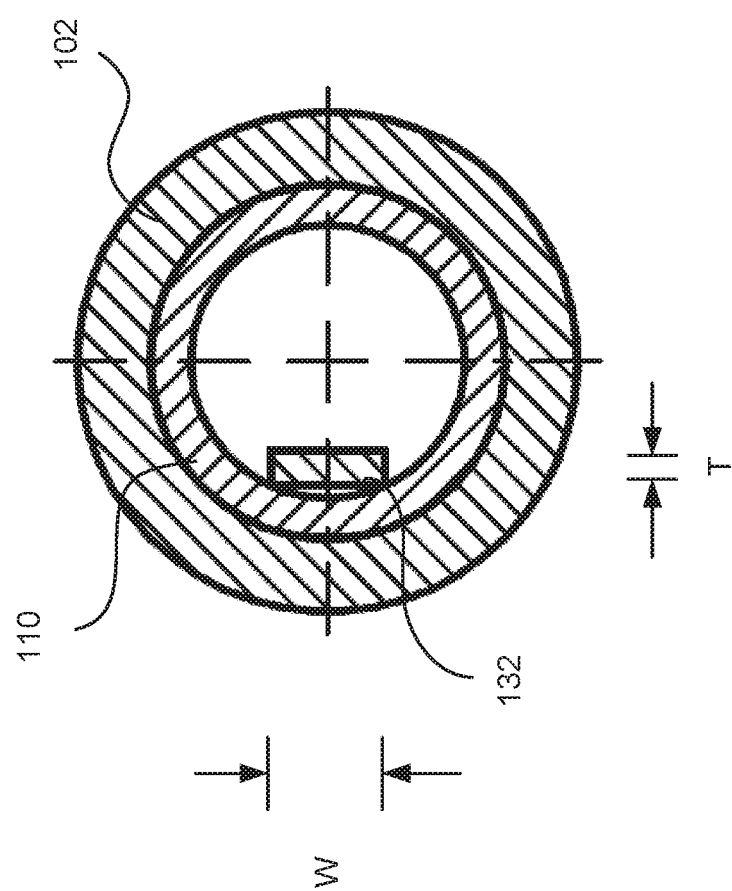
FIG. 3 is a cross-sectional view of the conductive tip catheter of FIG. 1, taken along section line A-A.

FIG. 3 is a cross-sectional view of the conductive tip catheter 100 of FIG. 1, taken at along section line A-A. As illustrated in FIG. 3, a center axis of the safety ribbon 132 may be offset from a center axis of the flexible tubular member 102 and/or metallic coil 110. The safety ribbon 132 may have a width W and thickness T substantially less than an inner diameter of the metallic coil 110.

Figure 4:
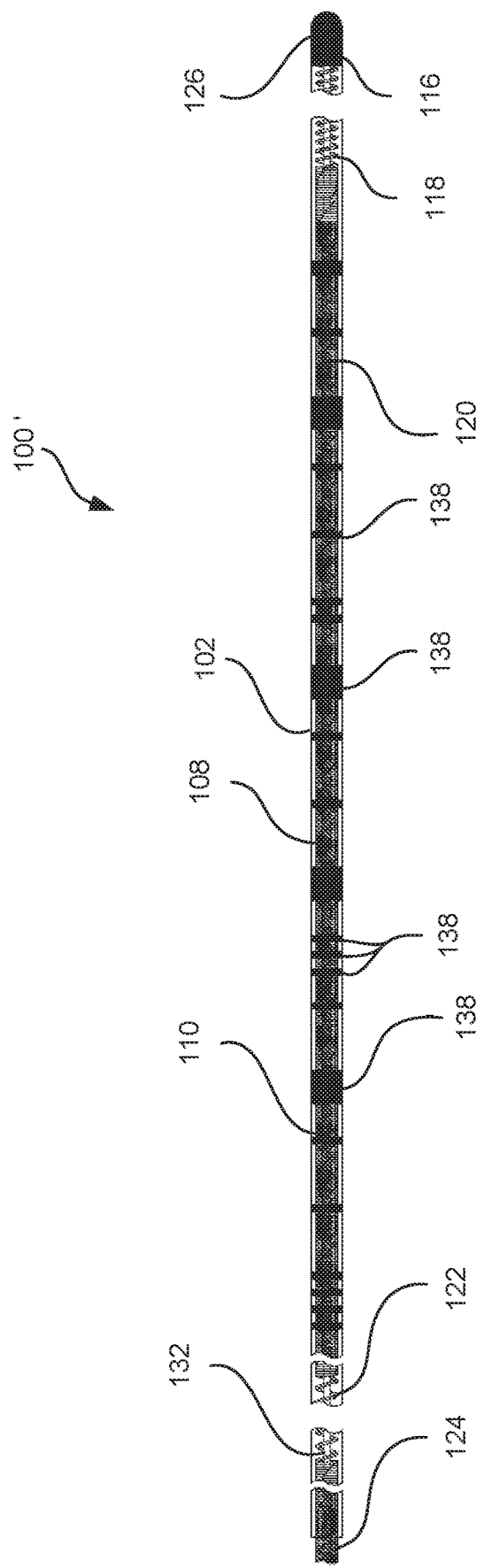
FIG. 4 is a side view of a conductive tip catheter according to an aspect of the present disclosure.

FIG. 4 illustrates a conductive tip catheter 100', according to an aspect of the present disclosure. The conductive tip catheter 100' may correspond to a version of the conductive tip catheter 100 illustrated in FIGS. 1-3 that includes a plurality of depth markers 138. The depth markers 138 are located on an exterior surface of the flexible tubular member 102. In some aspects, the depth markers 138 may be located on the metallic coil 110. For example, some of the coils of the metallic coil 110 can be visually distinguished from one another. The depth markers 138 may be printed on the flexible tubular member 102 and/or metallic coil 110 using non-toxic inks. The depth markers 138 may indicate a depth of insertion of the conductive tip catheter 100 into a patient. The depth markers 138 may have varying widths, such as between 1 mm and 10 mm. As illustrated in FIG. 4, the depth markers 138 may be located on the portion of the flexible tubular member 102 that overlaps with the third region 120 of the metallic coil 110. In other aspects, the depth markers 138 may be located on other regions of the flexible tubular member 102.

While a conductive tip catheter has been described in terms of what may be considered to be specific aspects, the disclosure need not be limited to the disclosed aspects. Additional modifications and improvements of the present disclosure may be apparent to those skilled in the art. This disclosure is intended to cover various modifications and similar arrangements included within the spirit and scope of the claims, the scope of which should be accorded the broadest interpretation so as to encompass any such modifications and similar structures. The present disclosure should be considered as illustrative and not restrictive.

What is claimed is:

1. A conductive tip catheter, comprising:
  a flexible tubular member comprising a proximal end and a distal end, the flexible tubular member defining a lumen extending between the proximal end and the distal end;
  an electrically conductive metallic coil at least partially located within the lumen of the flexible tubular member, the electrically conductive metallic coil comprising:

a first region located at a distal end of the metallic coil and having a first pitch, wherein the first region extends distally from the distal end of the flexible tubular member;
a second region proximal to the first region and having a second pitch that is greater than the first pitch; and
a third region proximal to the second region and having a third pitch that is different from the first pitch and the second pitch; and
a conductive tip located at the distal end of the flexible tubular member, the conductive tip defining a tip lumen in fluid communication with the lumen, wherein the conductive tip comprises a conductive polymer being carbon-filled polyurethane.

2. The conductive tip catheter of claim 1, wherein the conductive tip is welded to the first region of the electrically conductive metallic coil.

3. The conductive tip catheter of claim 2, wherein the conductive tip is welded over the first region of the electrically conductive metallic coil.

4. The conductive tip catheter of claim 3, wherein the conductive tip is radio frequency welded over the first region of the electrically conductive metallic coil.

5. The conductive tip catheter of claim 1, wherein an inner diameter of the tip lumen is smaller than an outer diameter of the first region of the electrically conductive metallic coil.

6. The conductive tip catheter of claim 1, wherein an inner diameter of the tip lumen is equal to an outer diameter of the first region of the electrically conductive metallic coil.

7. The conductive tip catheter of claim 1, wherein the flexible tubular member comprises polyurethane.

8. The conductive tip catheter of claim 1, further comprising a safety ribbon located within the lumen of the flexible tubular member.

9. The conductive tip catheter of claim 8, wherein the safety ribbon comprises a metallic wire.

10. The conductive tip catheter of claim 8, wherein the safety ribbon is coupled to the electrically conductive metallic coil at a distal region of the electrically conductive metallic coil and a proximal region of the electrically conductive metallic coil.

11. The conductive tip catheter of claim 1, wherein the flexible tubular member further comprises a plurality of depth markers on an exterior surface of the flexible tubular member.

12. The conductive tip catheter of claim 1, wherein the conductive tip has a rounded distal end.

13. The conductive tip catheter of claim 1, wherein a proximal end of the electrically conductive metallic coil extends proximally from the proximal end of the flexible tubular member.

14. The conductive tip catheter of claim 13, wherein the proximal end of the electrically conductive metallic coil is connected to an electrical current source.

15. The conductive tip catheter of claim 1, wherein the electrically conductive metallic coil directly connects to the flexible tubular member at each point of contact between the electrically conductive metallic coil and the flexible tubular member.

16. The conductive tip catheter of claim 1, wherein the third pitch is less than the second pitch.

17. The conductive tip catheter of claim 1, wherein the third pitch is greater than the first pitch.

18. The conductive tip catheter of claim 1, wherein the electrically conductive metallic coil further comprises a fourth region proximal to the third region and having a fourth pitch that is greater than the third pitch.

19. The conductive tip catheter of claim 18, wherein the electrically conductive metallic coil further comprises a fifth region proximal to the fourth region and having a fifth pitch that is less than the fourth pitch.

20. The conductive tip catheter of claim 1, wherein a proximal end of the conductive tip catheter is connected to a fluid source in fluid communication with the lumen of the flexible tubular member.

21. The conductive tip catheter of claim 20, wherein the fluid source is an anesthetic.

22. A conductive tip catheter, comprising:
a flexible tubular member comprising a proximal end and a distal end, the flexible tubular member defining a lumen extending between the proximal end and the distal end;
an electrically conductive metallic coil at least partially located within the lumen of the flexible tubular member, the metallic coil comprising:
a first region located at a distal end of the metallic coil and having a first pitch;
a second region proximal to the first region and having a second pitch that is greater than the first pitch; and
a third region proximal to the second region and having a third pitch that is less than the second pitch;
a conductive tip made from carbon-filled polyurethane and welded over and around the first region of the metallic coil through radio frequency welding, the conductive tip defining a tip lumen in fluid communication with the lumen; and
a safety ribbon located within the lumen of the flexible tubular member, the safety ribbon coupled to the electrically conductive metallic coil at a distal region of the electrically conductive metallic coil and a proximal region of the electrically conductive metallic coil,
wherein the electrically conductive metallic coil directly connects to the flexible tubular member at each point of contact between the electrically conductive metallic coil and the flexible tubular member.

* * * * *